United States Patent [19]
Klein et al.

[11] Patent Number: 4,869,596
[45] Date of Patent: Sep. 26, 1989

[54] THERMALLY CHECKING THE STATE OR THE CONDITION OF A HYDRAULIC FLUID

[75] Inventors: Hans-Christof Klein, Hattersheim; Peter Lohberg, Friedrichsdorf, both of Fed. Rep. of Germany

[73] Assignee: Alfred Teves GmbH, Frankfurt am Main, Fed. Rep. of Germany

[21] Appl. No.: 277,491

[22] Filed: Nov. 29, 1988

Related U.S. Application Data

[63] Continuation of Ser. No. 121,432, Nov. 17, 1987, abandoned.

[30] Foreign Application Priority Data

Nov. 20, 1986 [DE] Fed. Rep. of Germany ....... 3639664

[51] Int. Cl.$^4$ ...................... F16D 66/00; G01N 25/10
[52] U.S. Cl. ..................................... 374/27; 73/27 R; 188/1.11
[58] Field of Search ............................ 374/54, 27, 613; 364/426, 557; 340/52 B, 57; 73/27

[56] References Cited

U.S. PATENT DOCUMENTS

| | | | |
|---|---|---|---|
| 4,408,902 | 10/1983 | Peuker .................................... | 374/27 |
| 4,484,822 | 11/1984 | Hancock ................................. | 374/27 |
| 4,559,813 | 12/1985 | Brekelmans ........................... | 73/61.4 |
| 4,566,805 | 1/1986 | Klein et al. ............................ | 374/16 |
| 4,589,277 | 5/1986 | Collins et al. ......................... | 73/61.3 |

FOREIGN PATENT DOCUMENTS 2721232 11/1978 Fed. Rep. of Germany ........ 374/27

*Primary Examiner*—Daniel M. Yasich
*Attorney, Agent, or Firm*—Robert P. Seitter

[57] ABSTRACT

A method and device are disclosed for determining and checking a state or condition of a hydraulic fluid contained in a brake system, including a state of hydration and/or age such that the fluid boiling point is reduced. The boiling point or a characteristic value of the fluid which depends on the boiling point, on the one hand, and the instantaneous temperature value of the fluid, on the other hand, are measured by means of sensor elements. These two values represent a range of permissible comparative temperature values, including a thermal reserve which is within that same range and is determined for further permissible heating of the fluid. A warning signal is released when a predetermined minimum value of the thermal reserve is reached. The sensor elements have hollow spaces with open walls permitting fluid flow-through and have such a design as to ensure that, after heating-up, there comes about a stable cellular convection in a temperature range lying below the boiling temperature. The cellular convection is used as an indication of the condition or the state of the fluid.

16 Claims, 3 Drawing Sheets

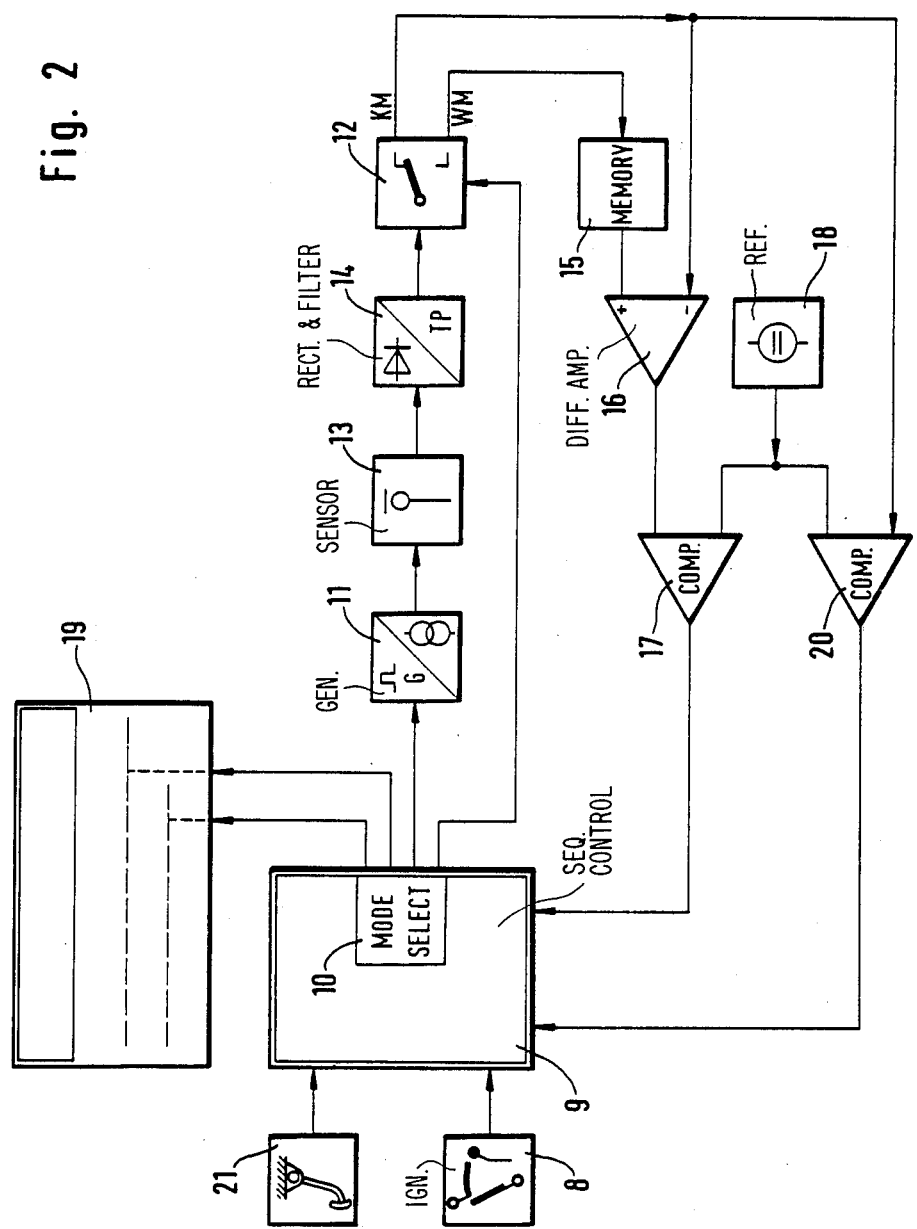

THERMALLY CHECKING THE STATE OR THE CONDITION OF A HYDRAULIC FLUID

This application is a continuation of application Ser. No. 07/121,432 now abandoned, filed 11-17-87.

BACKGROUND OF THE INVENTION

This invention relates to a method and to a device for determining and/or checking the state or the condition of a fluid contained in a hydraulic system such as a hygroscopic brake fluid. More particularly, the invention relates to a method and device for determining the boiling point or a characteristic of the fluid dependent on the boiling point by means of sensor elements. The invention also relates to circuit configurations for implementing the method and for controlling the device.

It is already known to check the state of a hydraulic fluid, namely a hygroscopic brake fluid, by measuring the boiling point of the fluid. Due to unavoidable absorption of water, the boiling point of the fluid can drop in the course of time such that in case of hard braking, the heat induced into the fluid can cause the formation of vapor bubbles which impairs the operativeness of the brake.

Changing brake fluid after one or two years such as is presently recommended is not an optimal solution to the problem since the process of aging, and in particular the absorption of water and accompanying boiling point reduction caused thereby, depends on numerous parameters such as climate, air humidity, mode of operation, and condition of the brake system and thus varies within very wide limits. Further, even a fresh brake fluid does not guarantee that in case of a strong strain on the brakes, such as in case of a prolonged, continuous application, the temperature of the brake fluid will remain below the value where dangerous vapor bubbles can form.

Methods and devices for measuring the boiling temperature of a brake fluid in the workshop or in laboratories are likewise known. According to a German industrial standard, a relatively accurate measuring method is known. However, it can be implemented only by trained staff and with relatively great expenditure of time and expensive equipment.

In the European Patent Specifications Nos. 56 424 and 74 415, measuring methods and measuring probes are described which are immersed in the fluid to be examined and which heat up a small amount of the fluid and ascertain the temperature at the onset of boiling. There are doubts as to whether it is possible to determine the boiling point of a brake fluid with sufficient accuracy in this manner, because, in fact, only the temperature of the pertaining heating element can be determined, and not the boiling temperature of the fluid.

One method for determining the condition and the state of a hydraulic fluid is disclosed in German Patent Application No. P 35 22 774.5 (DE-OS 35 22 774), published Dec. 29, 1986 wherein a sensor element is heated such as to ensure that there comes about a stable cellular convection in a temperature range lying below the boiling temperature of the fluid. The temperature in this phase is then measured either directly or indirectly as a voltage drop across the sensor element which voltage drop is suitable as an indication of the boiling point of the fluid and allows a relatively accurate determination of the boiling temperature.

Likewise, disclosed in the German Published Patent Application (DE-OS) No. 33 17 638 (U.S. Pat. No. 4,566,805) is a device for checking the brake fluid which is stationarily built into the brake system. According to this Published Patent Application, the actual detector can be designed as a component of a bleeder screw.

SUMMARY OF THE INVENTION

It now is an object of this invention to overcome the disadvantages of the known methods and devices and to provide a method for checking the state or condition of a hydraulic fluid, in particular of a hygroscopic brake fluid, by means of which it is possible to recognize with a high degree of reliability when proper functioning is no longer ensured due to an instantaneous state or due to the condition of the hydraulic fluid contained in a hydraulic system. For example, the invention provides a method by which it is possible to recognize when, due to thermal stress, the temperature of the fluid in a hydraulic brake system is approaching closely the boiling point of the fluid.

The object is achieved according to the invention in a surprisingly simple and technically advanced manner by means of a method referred to above, the particular feature of which provides for the instantaneous state of interest and/or the instantaneous stress of interest on the fluid to be measured and compared with a known characteristic value. Accordingly, a so-called (instantaneous) thermal reserve is determined which constitutes a measure of further allowable stressability, for example, for the further permissible heating of the fluid. According to the invention, the reaching of a predetermined minimum value of thermal reserve is also signalled.

This invention thus is based on the premise that the boiling point of the fluid depending on its age, on the one hand, and on the instantaneous thermal stress, on the other hand, must be taken into consideration for assessing the state and the condition or the usability of a fluid. In contrast to a mere determination of the boiling point of the hydraulic fluid, due to the determination of the instantaneous "thermal reserve" it is possible to reliably recognize, for instance, in a brake system, whether under the prevailing conditions (i.e., the boiling point of the brake fluid and the thermal stress on the fluid by the braking operation) there exists the danger of the formation of vaor bubbles and, therefore, a possible impairment of the brake's operation. Not only is a necessary brake fluid change pointed out to the driver, but there is also an indication of a possible danger due to overstress of the brake and heating up of the brake fluid which may also occur with fresh brake fluid. The driver then can make allowance for this fact by changing his driving behavior to avoid a brake failure.

In one advantageous embodiment of the inventive method, at predetermined intervals, the characteristic value which is dependent on and indicative of the boiling temperature of the fluid is determined, stored in a memory, and compared with the last-stored characteristic value so as to determine the thermal reserve. For checking a brake fluid it may be expedient to determine and store the characteristic value by means of a measuring device stationed in the automotive vehicle when the vehicle's engine is started. Preferably, the measuring device essentially includes sensor elements and electronic circuits for evaluating the sensor signals. Upon the application of the brake, the stored characteristic value is compared with the instantaneous brake fluid's temperature so as to determine a thermal reserve.

According to another feature of the inventive method, during a braking operation, the characteristic value and the instantaneous temperature of the brake fluid are measured alternately by means of a measuring device stationed in the vehicle, and the thermal reserve is determined by comparing the measured values.

According to an important aspect of the invention, a device for implementing this method is provided for essentially including a measuring device for determining the boiling temperature of the fluid, or alternatively a characteristic value depending on and indicative of the boiling temperature, temperature-measuring elements for determining the instantaneous temperature of the fluid, circuits for handling and processing the measured signals as well as for storing the characteristic values determined last and for determining an instantaneous thermal reserve as derived from the difference between the measured values, as well as indicating units for signalling a sufficient and/or an insufficient thermal reserve.

The measuring device for determining the characteristic value is equipped with one or with a plurality of sensor elements arranged in the fluid. In doing so, for determining the characteristic value, it is desirable to design the sensor elements so as to be able to be heated up.

The determination of the boiling temperature or of a characteristic value in relation to the boiling temperature is essential to the method and device of this invention. According to one aspect of the invention, the boiling temperature, or the characteristic value, is determined by means of a sensor element having a hollow space with open, flow-through walls and designed such as to ensure that, after heating up to a temperature range lying below the boiling temperature, there comes about a stable cellular convection evaluable as a criterion of the condition and/or the state of the fluid. The sensor element can be designed in the form of a hollow coil, perforated tube, a hollow body limited by grid-or-net-shaped boundary surfaces, or the like. The instantaneous temperature of the fluid can be determined by measuring the temperature-dependent electrical resistance of such a sensor element.

Heat-up sensor elements of the above-mentioned type wherein a stable cellular convection can be achieved are described in the German Published Patent Application No. 35 22 774.

According to a further embodiment of the inventive device, the sensor elements for heating up the fluid or for measuring the temperature of the fluid are supplied with alternating current. Accordingly, it is possible to avoid undesired electrolytic effects in the fluid to be examined.

The sensor elements for determining the instantaneous temperature and/or the characteristic value depending on the boiling temperature are expediently arranged in a vehicle's brake system in the wheel brake cylinders or in the proximity thereof. On the other hand, it is also possible to arrange the sensor element for determining the instantaneous temperature in the wheel brake cylinder and to arrange the sensor element for determining the characteristic value in the pressure medium compensation/storage reservoir of the brake system.

Further, one embodiment of the invention provides for the same sensor elements to be used both for determining the boiling temperature, or the characteristic value, and for measuring the instantaneous temperature.

Upon the starting of the automatic vehicle's engine, a circuit configuration for implementing the method of this invention and for controlling a corresponding device serving to check the brake fluid in the vehicle's brake system measures the boiling temperature of the brake fluid or the corresponding characteristic value and stores the measured result until a new start of the engine. During the application of the brake the same sensor element determines the temperature of the fluid so as to determine the instantaneous thermal reserve.

Upon the application of the brake pedal, according to another embodiment of the inventive circuit configuration, the boiling temperature, or the characteristic value of the brake fluid, and the momentary temperature of the brake fluid are measured by means of the same sensor elements and the successive values measured are compared so as to determine the instantaneous thermal reserve.

According to an important feature of the invention, the individual sensor elements are operated in the so-called hot mode, on the one hand, and in the so-called cold mode, on the other hand. In the hot mode, the sensor elements are operated as heating filaments or heating coils or the like and are electrically heated up so as to cause a cellular convection in the area of the sensor elements and to enable the determination of the boiling point or of the corresponding characteristic value. In the hot mode, too, the boiling temperature or the temperature at which the cellular convection occurs is determined by measuring the electrical temperature-dependent resistance of the sensor element. In the cold mode, the sensor elements are fed a comparatively very low current which does not effect any heat, but only permits measurement of the electrical resistance of the sensor element, which electrical resistance depends on the temperature of the surrounding fluid. Thus, in the cold mode the sensor elements serve as mere temperature-measuring elements.

BRIEF DESCRIPTION OF THE DRAWING

Further characteristics, advantages, and applications will become evident from the following description, reference being made to the accompanying Drawings in which:

FIG. 2 is a block diagram of a circuit configuration for implementing the inventive method and for operating a device according to the invention.

DETAILED DESCRIPTION OF A PREFERRED EMBODIMENT

Figure 1A:
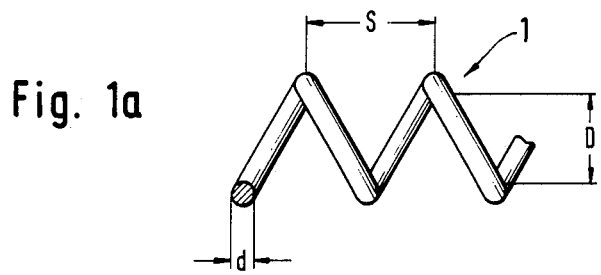
FIGS. 1a, 1b, 1c, 1d and 1e are pictorial views of sensor elements which provide cellular convection to be achieved in the hot mode.

FIG. 1a shows a particularly simple embodiment of a sensor element for implementing the method and for constructing a device according to this invention. In this embodiment, the sensor element 1 is a hollow coil which is wound from a solid-core (90%/10%) platinum-and-iridium wire. The wire diameter "d", for instance is 50 micrometers, the coil diameter "D" is 200 micrometers, and the pitch "S" is 240 micrometers. The entire sensor element, only part thereof being shown in FIG. 1a, has about 20 windings. The cold resistance, that is the resistance at room temperature of this sensor has been found to be about 2.3 ohms. By means of an alternating current of about 700 milliamperes it is possible to heat up the sensor element 1 hollow coil until there results a cellular convection. While in the heat-up phase, the electrical resistance was found at first to rise steeply with the formation of a cellular convection discernible by the transition of the resistance curve into an approximatively constant gradient. This has been described in detail in the above-mentioned German Published Patent Application (DE-OS) No. 35 22 774. The amount of the electrical resistance of the hollow coil, or rather of the sensor element 1, in the range of cellular convection permits a determination of the boiling temperature of the examined brake fluid with great accuracy and, thus, gives an accurate indication as to the state and condition of the fluid. Further heating of the sensor beyond the phase of cellular convection does not provide at reasonable expense any reproducible resistance variation in dependence on the supplied current which can be evaluated as a measured value.

Figure 1B:
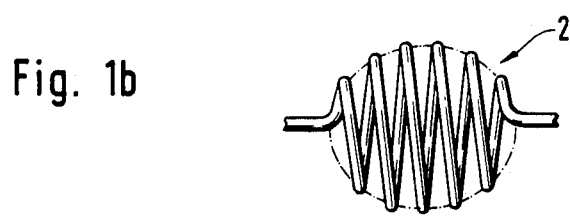
Figure 1C:
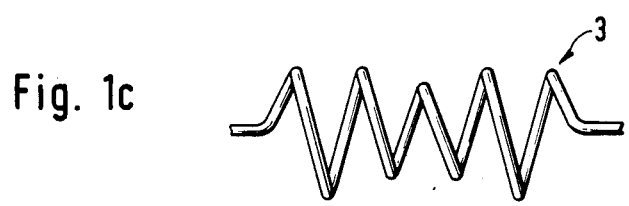
Figure 1D:
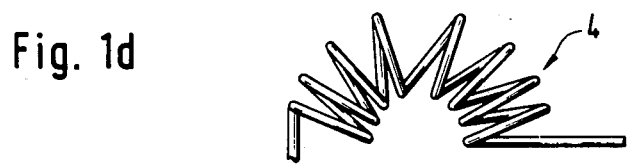

FIGS. 1b, 1c, and 1d show further hollow-coil-shaped or hollow-coil-type configurations 2, 3, and 4 which may be made from the same wire as the sensor element 1 according to FIGS. 1(a)–(l) which likewise result in a stable cellular convection near the boiling point of the fluid.

Figure 1E:
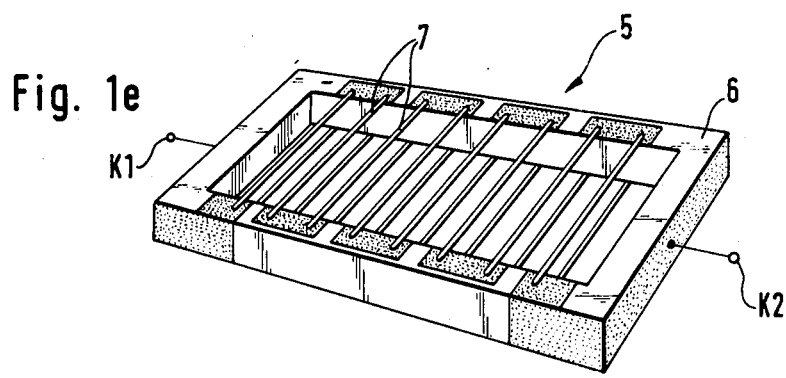

FIG. 1e shows an embodiment of a sensor element 5 which can be used instead of the coils of FIGS. 1a through 1d. The sensor element 5 has a frame-shaped supporting body 6 made of ceramics, for instance, and serves as a substrate for a heating filament 7 applied thereto in a meander-shaped or grid-shaped manner. The heating filament 7 thus forms a cell comparable to the above hollow-coil-type configurations, and likewise permits a stable cellular convection of fluid during sensor operation. The sensor element 5 is connected to the power source through the terminals K1, K2.

The inventive device essentially consists of at least one or, if desired, a plurality of the sensor elements 1, 2, 3, 4, 5 of the type represented in FIG. 1(a)–(l) and of an electronic circuit configuration by means of which preferably alternating current can be supplied to the sensor elements and by means of which the measured signals can be derived and evaluated. Expediently, the sensor elements are arranged in all wheel brake cylinders, or alternatively in the proximity thereof, and in any case at least in the wheel brakes stressed most. Also suitable for determining the boiling point or the corresponding characteristic value of the fluid is a sensor element arranged in another location such as in a pressure medium storage reservoir.

In principle, the boiling point of the fluid, on the one hand, and the momentary or instantaneous thermal stress which in particular demands on the heating up of the fluid during a braking operation, on the other hand, are measured and compared with each other by means of the inventive method and the corresponding device. A so-called momentary thermal reservie is derived from the measured values. The momentary thermal reserve reveals whether in case of further thermal stress, or in case of further increase in the fluid's temperature, formation of vapor bubbles will occur due to the boiling point being approached and, accordingly, whether the brake's operation will be endangered. The thermal reserve thus is a value signalling that an available residual thermal absorption capacity has been surpassed.

With regard to the dangerous formation of vapor in the brake cylinder, it is very difficult to determine the exact relation between the thermal absorption capacity of brake fluids of varying composition and the brake performance realized out of different driving situations. Therefore, certain safety thresholds are derived from empirical values and the thermal reserve is defined as follows:

$$\text{THERMAL RESERVE} \approx (T_{permissible} - T_{actual})$$

In this definition, $T_{permissible}$ is a permissible limit temperature of a brake fluid and $T_{actual}$ is the momentary or instantaneous temperature of the brake fluid reached during the braking operation.

If the THERMAL RESERVE drops below a value derived from experience then the THERMAL RESERVE is used up. This will be signalled to the driver. By treating the brake gently or by taking other measures for cooling down the brake fluid the driver then may counteract the danger of vapor bubbles forming. If the thermal reserve is used up prematurely, such as in case of relatively sparse brake application, this indicates that there is some trouble in the brake system or that the brake fluid has aged excessively.

Figure 3:
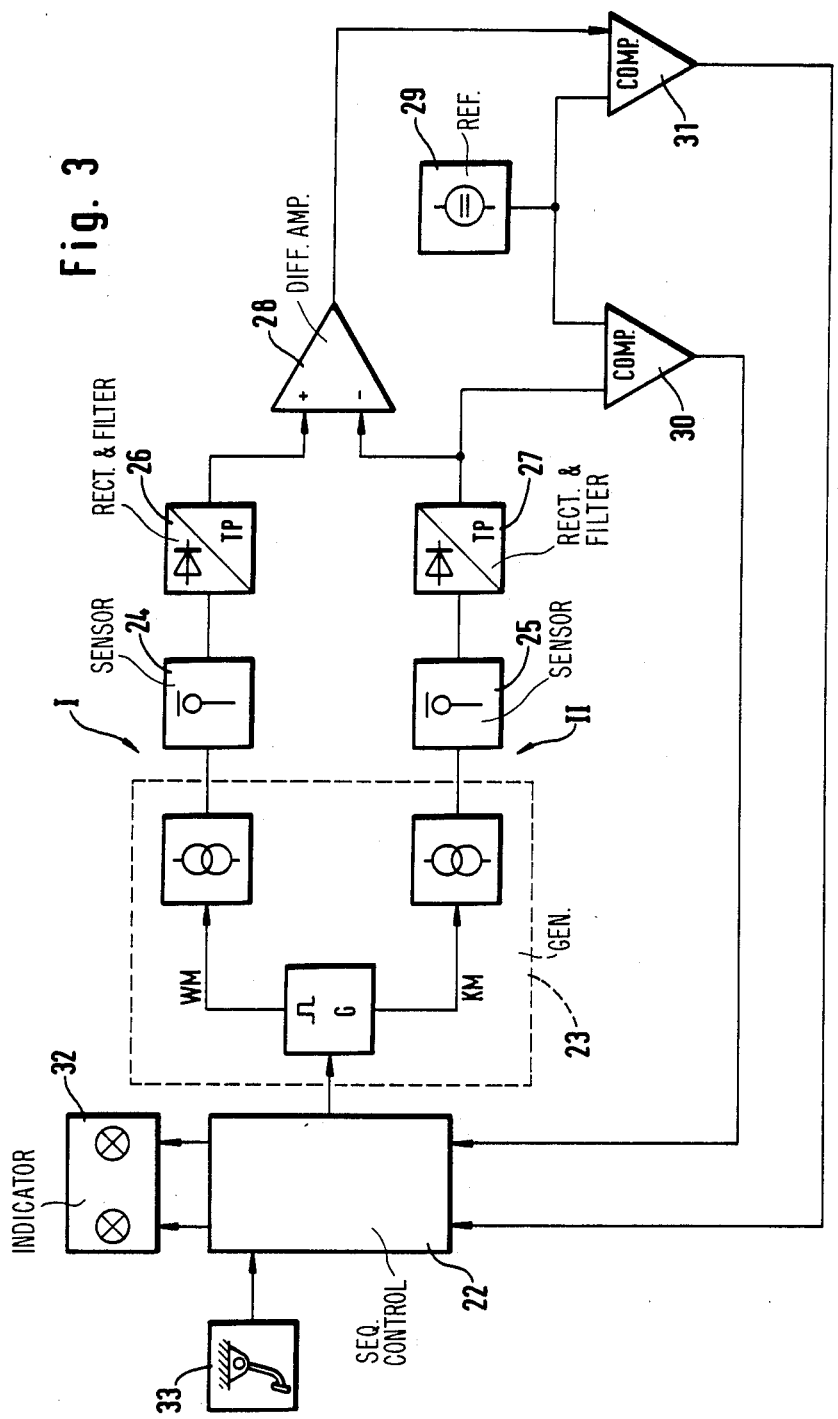
FIG. 3 is a block diagram of another embodiment of the circuit configuration of FIG. 2.

The two circuit configurations of FIGS. 2 and 3 serve to explain different measuring principles within the scope of this invention. Both circuit configurations are provided for checking the brake fluid in automotive vehicle brake systems.

When using the circuit configuration of FIG. 2 the process sequence is initiated at certain time intervals, for instance, each time the ignition switch 8 (IGN.) of an automotive vehicle's engine is actuated. The signal produced the the switch 8 is fed to a sequencing control and logic 9 (SEQ. CONTROL) which may contain hardwired circuits or a program-controlled circuit such as a microcomputer. At first, a measurement is performed in the hot mode. Therefore the circuit 9 is equipped with a mode selector circuit 10 ("MODE SELECT"). The signal of circuit 10 switches on a generator 11 (GEN.) and simultaneously brings a switch 12 into the WM position (WM=hot mode). The generator 11 generates an alternating current of constant amplitude. In practice, such a generator is realized by means of a power operational amplifier, or by an operational amplifier and a power transistor operated as a voltage-controlled current source. By switching over the voltage levels at the input of the generator 11 by means of the sequencing control 9, the operating currents are generated for implementing the measurements in the hot and cold modes. According to one embodiment of this invention, 700 milliamperes are provided for the hot mode measurements and 7 milliamperes are provided for the cold mode.

The current source, namely the generator 11, supplies a sensor element 13 (SENSOR) having the design of one of the sensor elements 1–5 represented in FIGS. 1(a)–(l). By using alternating current, undesired electrolytic effects are prevented which might lead to the dissolution of the fluid to be measured.

The output signal of the sensor 13 is handled in a subsequent rectifier-and-filter stage 14 (RECT. & FILTER). The measured signal obtained in the hot mode is stored in a memory 15 until a subsequent hot mode measurement.

Subsequently, the selector circuit 10 switches back the switch 12 into the KM position (KM=cold mode) and switches back the generator 11 which now only emits a very low current needed for the cold mode measurement. The signal measured in the cold mode is continuously subtracted from the memory's 15 output signal in a differential amplifier stage 16 (DIFF. AMP.) representing the hot-mode-measured result and the difference signal is compared with a reference signal generated in the source 18 (REF.) in a comparator 17 (COMP.). The reference signal, or the output signal of the stage 18, is a measure of the minimal thermal reserve to be maintained for safety reasons. If there is a drop below the minimum value, a warning signal is given by means of the logic 9 and by means of an indicating unit 19.

As shown in FIG. 2, the output signal of the reference stage 18 is also used for checking the signal generated in the cold mode. To this end, the comparator 20 is provided. If the sensor element 13 is intact, the KM signal must move within a certain "window". This is checked by the comparator 20 whose output signal likewise is supplied to the logic 9 and will cause a warning to be displayed in the indicating unit 19.

In practice, the assemblies 11, 12, 13, 14 can be accomplished most easily by analogue units while the digital technique offers itself for the functions of the stages 15, 16, 17, 18, 20. The use of a corresponding programmed microcomputer is likewise suitable.

It is also possible to initiate the sequence control—in particular the cold mode measurements—only after the brake has been applied. This is expressed by the symbolic illustration of a brake pedal 21 signalling a brake application to the sequencing control 9.

In contrast to the sequence described with reference to FIG. 2, in the embodiment of the circuit according to FIG. 3, the signals obtained in hot mode and in cold mode are processed in parallel. In this embodiment, the output of a sequencing control and logic 22 (SEQ. control) leads to a generator 23 (GEN.) simultaneously generating the alternating currents needed in the hot mode and cold mode. By way of parallel signal paths I, II each equipped with their own sensor elements 24 and 25 (SENSOR) and subsequent signal processing stages 26 and 27 RECT. & FILTER (rectifier-and-filter circuits), the measured signals can be generated and processed in parallel in the hot mode (branch I) and in the cold mode (branch II). The measured results are then compared in a differential amplifier stage 28 (DIF. AMP) and the thermal reserve is determined whose minimum value again is predetermined by stage 29 (REF.) which generates a reference signal. The reference signal is combined with the difference signal (output signal of the amplifier 28) and with the measured signal obtained in the cold mode by the comparator stages 30 and 31 (COMP.). The output signals of the comparators 30, 31 are supplied to the sequencing control and logic 22. An indicating unit 32 is connected to the sequencing control and logic 22. Troubles in the system as well as whether the minimum thermal reserve has been reached cause a warning to be displayed at the indicating unit 32.

When the brake is applied, an actuating signal is supplied by the brake pedal 33 to the sequencing control 22.

For implementing the sequence described with reference to FIG. 3, in most cases it is sufficent to locate the sensor element 24 for the determination of the hot mode in the usual pressure medium storage/pressure compensation reservoir of the brake system while the sensor element(s) 25 for measuring the instantaneous fluid temperature are arranged in the wheel brakes of the wheels stressed most.

It is likewise possible to combine the modes of operation of the circuit configurations of FIGS. 2 and 3.

What is claimed is:

1. A method for determining the state or condition of a fluid contained in a hydraulic brake system, in a vehicle wherein said fluid has a boiling point, a temperature and a characteristic value in relation to the boiling point, said characteristic value being a resistance value measured according to a current and being determinable by means of a sensor element in said system, the method comprising determining an instantaneous thermal state of the fluid with sensor elements located in said system, measuring the instantaneous temperature and the characteristic value, determining from a comparison of said measurements of the instantaneous temperature and characteristic value, an instantaneous thermal reserve of the fluid in the system, said instantaneous thermal reserve being a value that is the difference between a predetermined stored temperature value of the fluid and the actual temperature of the fluid during braking operation, and emitting a warning signal when said instantaneous thermal reserve coincides with a predetermined minimum value.

2. The method as claimed in claim 1 wherein at predetermined intervals, the characteristic value is determined and stored in a memory and said instantaneous temperature of the fluid is compared with said stored characteristic value so as to determine the thermal reserve.

3. The method for checking the state of the brake fluid contained in an automotive vehicle's brake system, as claimed in claim 2, wherein, upon the starting of the vehicle's engine, the characteristic value is determined and stored by means of a measuring device provided in the automotive vehicle, said measuring device comprising a plurality of sensor elements for measuring instantaneous temperature of the fluid and electronic circuit means for evaluating signals from the sensor elements and for storing said characteristic value and for determining a momentary thermal reserve, said method comprising, upon application of the brake, the characteristic value and the instantaneous temperature of the brake fluid are measured alternatingly by means of a measuring device stationed in the vehicle.

4. The method for checking the state of a brake fluid contained in an automotive vehicle's brake system, as claimed in claim 2, wherein during a braking operation, the characteristic value and the instantaneous temperature of the brake fluid are measured alternatingly by means of a measuring device comprising at least one sensor element which is stationed in the vehicle.

5. A device for determining the state or condition of a fluid in a hydraulic system in a vehicle comprising measuring means for determining the boiling temperature of the fluid by defining a characteristic value in relation to the boiling temperature; said measuring means including at least one temperature-measuring sensor element for measuring the instantaneous temperature value of the fluid; electrical circuit means for handling and processing measured signals from said temperature-measuring sensor element, for storing said characteristic value and for determining a momentary instantaneous thermal reserve of the fluid in the system; and indicating means for signalling a sufficient or an insufficient thermal reserve as measured by said electrical circuit means; said characteristic value being measured by a current and being determinable by means of said temperature-measuring sensor element; and said instantaneous thermal reserve being a value that is the difference between a predetermined stored temperature limit value of the fluid and the actual temperature of the fluid during braking operation.

6. The device as claimed in claim 5 wherein the measuring means for determining the boiling point and the characteristic value related to the boiling point, is equipped with a plurality of sensor elements positioned in the fluid.

7. The device as claimed in claim 6 wherein the sensor elements for determining the boiling point and the characteristic value, can be heated up.

8. The device as claimed in claim 7 wherein the sensor elements have hollow spaces with open, flow-through walls and are designed such as to ensure that, after heating up, there comes about a stable cellular convection in a temperature range lying below the boiling temperature, said cellular convection being an indication of the state or the condition of the fluid.

9. The device as claimed in claim 8 wherein the sensor elements are designed in the form of hollow coils, perforated tubes, hollow bodies limited by grid-or-net-shaped-like boundary surfaces.

10. The device as claimed in claim 6 wherein the electrical circuit means includes means for measuring a temperature-dependent electrical resistance of the sensor elements, said measured temperature dependent electrical resistance representing the instantaneous temperature of the fluid.

11. The device as claimed in claim 6 wherein the sensor elements are supplied with an alternating current to heat up said sensor elements, said heating of said sensor elements resulting in a convection current which causes a heating up of the fluid, whereby said sensor elements measure the temperature of the fluid.

12. The device as claimed in claim 6 wherein the device is provided for checking the condition of a brake fluid contained in a brake system the sensor elements for determining the instantaneous temperature of the fluid are positioned in wheel brake cylinders of the system or in close proximity to the wheel brake cylinders.

13. The device for checking the brake fluid contained in a vehicle as claimed in claim 6 wherein sensor elements for determining the instantaneous temperature are positioned in the individual wheel brake cylinders or in close proximity thereto and said sensor elements for determining the characteristic value related to the boiling temperature of the fluid are positioned in a pressure medium storage reservoir of a brake system.

14. The device as claimed in claim 6 wherein a common sensor element can be used both for determining the characteristic value related to the boiling temperature and for measuring the instantaneous temperature.

15. The device as claimed in claim 5 wherein the electrical circuit means, upon starting of a vehicle's engine, measures the boiling temperature of the fluid and the characteristic value related to the boiling temperature, and stores said value until a subsequent start of the engine and during operation of the hydraulic brake system, said circuit means by means of said at least one measuring element determining the instantaneous temperature of the fluid and comparing said instantaneous temperature with the stored measured value to determine the thermal reserve.

16. The device as claimed in claim 5 wherein the temperature-measuring element and the electrical circuit means, upon operation of a brake pedal, alternatingly determines the boiling temperature of the fluid and the characteristic value, and the instantaneous temperature of the fluid and said electrical circuit means compares successively obtained measured values to determine the thermal reserve.

* * * * *